(12) United States Patent
Liu et al.

(10) Patent No.: US 6,388,750 B1
(45) Date of Patent: May 14, 2002

(54) DEVICE AND METHOD FOR PRELIMINARY TESTING A NEAT SERUM SAMPLE IN A PRIMARY COLLECTION TUBE

(75) Inventors: Yangang Liu, Irvine; Tung Rung Wang, Fullerton; Ian Nguyen, Corona, all of CA (US); Shirley Pfeifer, Laramie, WY (US); Jack McNeal, Long Beach, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/213,736

(22) Filed: Dec. 17, 1998

(51) Int. Cl.[7] ................................................. G01N 21/59
(52) U.S. Cl. ....................................... 356/436; 356/246
(58) Field of Search ................................. 356/436, 441, 356/442, 409, 414, 379, 246; 250/577

(56) References Cited

U.S. PATENT DOCUMENTS

| | | |
|---|---|---|
| 2,566,789 A | 9/1951 | Blackinton et al. .............. 88/1 |
| 3,263,554 A | 8/1966 | Pickels |
| 3,573,470 A | 4/1971 | Haley |
| 3,781,116 A | 12/1973 | Jones |
| 4,169,125 A | 9/1979 | Rodriguez et al. |
| 4,240,751 A * | 12/1980 | Linnecke et al. ........... 358/409 |
| 4,440,497 A | 4/1984 | Carey et al. |
| 4,456,581 A | 6/1984 | Edelmann et al. |
| 4,588,893 A | 5/1986 | Vidrine et al. |
| 4,728,190 A | 3/1988 | Knollenberg |
| 5,181,082 A | 1/1993 | Jeannotte et al. |
| 5,241,368 A | 8/1993 | Ponstingl et al. |
| 5,314,825 A | 5/1994 | Weyrauch et al. |
| 5,407,638 A | 4/1995 | Wang |
| 5,561,069 A | 10/1996 | Bringham-Burke et al. |
| 5,705,815 A | 1/1998 | Heesch ..................... 250/341.2 |
| 5,734,468 A * | 3/1998 | McNeal ...................... 356/319 |
| 5,831,268 A * | 11/1998 | Morita et al. ............. 250/341.8 |

FOREIGN PATENT DOCUMENTS

| | | | |
|---|---|---|---|
| WO | WO97/19339 | 5/1997 | .......... G01N/21/03 |
| WO | WO97/19340 | 5/1997 | .......... G01N/21/27 |

* cited by examiner

*Primary Examiner*—Richard A. Rosenberger
(74) *Attorney, Agent, or Firm*—William H. May; Gary T. Hampson; Hogan & Hartson, LLP

(57) ABSTRACT

A device and method for performing a preliminary test on a neat serum sample contained in a primary collection tube is provided herein. The method includes the steps of positioning of an optical probe near the primary collection tube and monitoring the neat serum sample in the primary collection tube to determine whether an interferant, such as hemolysis, icteris and lipemia are present in the serum sample. From this test, a hemolytic index, an icteric index and a lipemic index can also be established for the neat serum sample. Based upon these serum indices, the neat serum sample can be transferred to a clinical analyzer for additional testing or to waste receptacle because the sample is compromised. Additionally, a volume test can be performed on the serum sample in the primary collection tube so that the serum sample can be properly allocated during subsequent testing.

29 Claims, 6 Drawing Sheets

DEVICE AND METHOD FOR PRELIMINARY TESTING A NEAT SERUM SAMPLE IN A PRIMARY COLLECTION TUBE

FIELD OF THE INVENTION

The present invention relates to a method and device for preliminary testing of a serum sample in a sample container. The present invention is particularly useful for establishing a hemolytic index, an icteric index and a lipemic index for a neat serum sample, prior to removing the neat serum sample from the primary collection tube. The present invention is also useful for evaluating whether sufficient serum sample is present in the primary collection tube.

BACKGROUND

The accurate analysis of a serum sample is often instrumental in determining the health of a patient and what measures are necessary to restore the health of the patient. In an effort to reduce laboratory labor costs, many hospitals and laboratories utilize automated clinical analyzers to analyze patient serum samples. Clinical analyzers are presently able to accurately and quickly perform such functions as drug monitoring, specific protein blood analysis and cancer detection on a serum sample.

These clinical analyzers commonly utilize a plurality of cuvettes which are sequentially subjected to a variety of tests during a machine cycle of the clinical analyzer. Typically, during a machine cycle, the testing begins at one location, samples are added at one location and multiple serum samples are sequentially tested.

In some cases, the integrity of the serum sample may affect the interpretation of the results of the clinical analyzer. For example, preanalytical variables in the serum sample, which are not related to the patient disease state, may cause a different interpretation of the condition of the patient. Preanalytical variables include hemolysis (ruptured red blood cells), Icteris (excessive Bilirubin) and Lipemia (high, visible lipid content).

One way to evaluate the integrity of the serum sample is to have a skilled laboratory worker visually inspect the color of the serum sample. A normal serum sample has a light yellow to light amber color. Alternately, a serum sample containing Hemolysis is reddish in color, a sample containing Icteris is dark yellow/brown in color and a sample containing Lipemia is whitish in color. Thus, the degree of red color in a serum sample corresponds to the amount Hemolysis present in the serum sample, the degree of dark yellow/brown color corresponds to the amount of Icteris present in the serum sample and the degree of whitish color corresponds to the amount of Lipemia present in the serum sample.

Typically, a laboratory worker will assign an hemolytic index, an icteric index and a lipemic index to the serum sample based upon the color. Based upon the value of the hemolytic index, the icteric index and the lipemic index, the interpretation of the results from the clinical analyzer can be evaluated. Alternately, if the value of one or more of the hemolytic index, the icteric index and the lipemic index are too high, the serum sample will be discarded without analysis by the clinical analyzer.

However, visual inspection can be labor intensive and costly. Further, the possibility of human error exists with visual inspection, the results of the visual inspection is highly subjective and varies between workers, and one of the variables could mask or hide the other variables. Furthermore, with closed container sampling, bar code labels directly on the container, and automated clinical analyzers, the laboratory worker, in many instances simply does not have an opportunity to visually observe the serum sample. Thus, it is becoming increasing important to evaluate the integrity of the serum sample without the use of visual inspection by a laboratory worker.

One attempt to solve this problem involves optically viewing the serum sample after the serum sample has been transferred to one of the cuvettes of the clinical analyzer. Measuring the optical characteristics of the sample in the clinical analyzer eliminates the need for visual inspection. However, this test utilizes machine time of the clinical analyzer and if the integrity of the serum sample is determined to be compromised, additional machine time and a machine cycle are wasted. Further, this procedure can not be used with clinical analyzers which add reagents to the cuvette prior to adding the serum sample.

Another attempt to solve the problem involves separately testing a portion of the serum sample in a separate cuvette of the clinical analyzer, simultaneously with the other tests being performed on the serum sample by the clinical analyzer. However, this requires the use of a portion of the sample and the clinical analyzer. Therefore, this procedure will waste sample and machine time. Further, with this procedure, if the serum sample is determined to be compromised, a machine cycle and reagents are wasted.

Yet another attempt to solve the problem involves evaluating the serum sample in a probe during the transfer of the serum sample. This device is discussed in detail in U.S Pat. No. 5, 734,468, issued to McNeal, the contents of which are incorporated herein by reference. Unfortunately, because the integrity of the sample is evaluated in the probe, the probe must be washed with a wash fluid to prevent carry-over between serum samples. For large scale operations, the wash fluid poses several problems, including increased costs and increased environmental concerns.

In light of the above, it is an object of the present invention to provide a method and device which evaluates the integrity of a serum sample, without visual inspection by a laboratory worker. Another object of the present invention is to provide a method and device which quickly and accurately determines the presence of Hemolysis, Icteris and Lipemia in a sample, without consuming any sample and without adversely effecting the integrity of the sample. Yet another object of the present invention is to provide a method and device which establishes a hemolytic index, an icteric index and a lipemic index for the serum sample, without wasting machine time of the clinical analyzer and without interrupting the operation of the clinical analyzer. Yet another object of the present invention is to provide a method and device which determines the presence of any interferant in the sample, without consuming the sample. Still another object of the present invention is to provide a method and device which evaluates the integrity of the sample and transfers the sample to an appropriate location based upon the integrity of the sample. Yet another object of the present invention is to provide a device and method for determining the amount of sample in the sample container available for testing with the clinical analyzer.

SUMMARY

The present invention is directed to a method and device for performing preliminary tests on a sample in a sample container which satisfies these objectives. The method includes the steps of (i) providing an optical probe; and (ii)

monitoring the sample in the storage container with the optical probe to determine the suitability of the sample for additional testing. The present invention is particularly suited for performing preliminary tests on a neat serum sample in a primary collection tube without removing the neat serum sample from the primary collection tube.

The preliminary tests include a screening test to evaluate the integrity of the sample in the sample container and/or a volume test to measure the amount of sample available for testing. Importantly, with the present invention, the sample is preliminarily tested in the storage container, prior to being removed from the storage container and prior to being transferred to a clinical analyzer. Therefore, machine time of the clinical analyzer is not wasted, the sample is not consumed or altered and the sample can be transferred to an appropriate location, e.g., the clinical analyzer or a waste receptacle, based upon results of the evaluation.

The following terms used in this application shall have the following meaning:

"Neat Serum Sample" shall mean undiluted serum or plasma.

"Primary Collection Tube" shall mean a blood collection tube used to collect blood from a patient. A suitable blood collection tube is manufactured by Becton Dickinson, located in Franklin Lakes, N.J.

"Serum Variables" shall mean and include hemolysis, icterus, lipemia and other variables, which may affect the accuracy of the results of the clinical analyzer.

"Interferant" shall mean and include any of the serum variables, any disease condition and/or any variable which may affect the interpretation of the results of the clinical analyzer and/or be of interest to the doctor or patient.

"Hemolytic index" shall mean the grade given to a particular sample based upon the estimated content of hemolysis present in the sample. Generally, the grading scale for visual observation ranges from zero through four (0–4). Zero represents substantially no hemolysis while four represents significant hemolysis. Alternately, the scale could be 0–10, 0–20, A–F or some other range.

"Icteric index" shall mean the grade given to a particular sample based upon the estimated content of icterus present in the sample. Generally, the grading scale for visual observation ranges from zero through four (0–4). Similarly, zero represents substantially no icterus, while four represents significant presence of icterus. Alternately, the scale could be 0–10, 0–20, A–F or some other range.

"Lipemic index" shall mean the grade given to a particular sample based upon the estimated content of lipemia present in the sample. Generally, the grading scale for visual observation ranges from zero through four (0–4). Similarly, zero represents substantially no lipemia, while four represents significant presence of lipemia. Alternately, the scale could be 0–10, 0–20, A–F or some other range.

"Serum Indices" shall mean and include the hemolytic index, the icteric index and the lipemic index.

"Predetermined Value" shall mean a value for the hemolytic index, the icteric index or the lipemic index at which the integrity of the sample for testing may be considered to be compromised. The predetermined value varies according to the scale of the serum indices, which of the serum indices is in question and the tests to be performed by the clinical analyzer or other device. For example, if the hemolytic index is rated on a scale of 0–4, a hemolytic index of 3 could be considered to compromise the sample for some tests. Thus, the predetermined value in this example would be 3. Alternately, a reading of 2 on a scale of 0–4for the icteric index could be unacceptable in some instances. Thus, for this example, the predetermined value is 2.

"Spectophotometric analysis" shall mean and include measuring optical absorbence and/or reflectance, a turbidimetric analysis, a nephelometric analysis, and/or light scatter analysis at any angle or collection of angles.

In a screening test, the optical probe can determine whether an interferant is present in the serum sample. Further, the optical probe can establish one or more of the hemolytic index, the icteric index and the lipemic index of the sample. This allows the laboratory to determine whether the sample is suitable for testing with the clinical analyzer and allows the results from the clinical analyzer to be properly evaluated. With the present invention, the serum variables and a serum indices are evaluated without consuming or altering the sample.

In a volume test, the optical probe evaluates the amount of sample available in the sample container. This allows the laboratory to properly allocate the sample for additional testing. For a volume test, the optical probe is positioned near the sample and is used to determine the location of an upper sample surface of the sample in the sample container. With the location of the sample surface and the shape of the container, the volume of sample in the sample container can be evaluated. Again, the sample is evaluated in the storage container, prior to being removed from the storage container.

Also, the method can include the step of transferring the sample to another location based upon the results of the preliminary tests on the sample. For example, the sample container and sample can be transferred to a waste receptacle, if one of the serum indices is above the predetermined value or the sample container and sample can be transferred to a clinical analyzer for additional testing or a sample splitter if all of the serum indices are below the predetermined value.

The invention is also directed to a device for performing a preliminary test on the sample. The device includes an optical probe having a probe body, a collector, and a detector. A probe tip of the probe body is positioned near the sample container. The collector receives information about the sample. This information is transferred to the detector, which performs the preliminary tests on the sample based upon information received by the collector.

It is important to recognize that with the present invention, the integrity of a neat serum sample can be tested within a primary collection tube, without using a laboratory worker and without removing the neat serum sample from the primary collection tube. Additionally, the present invention quickly and accurately determines the level of the serum indices, without consuming any of the neat serum sample and without adversely effecting the integrity of the neat serum sample. Furthermore, the optical probe can measure the amount of sample in the storage container to ensure that enough sample exists for testing before transferring the sample to the clinical analyzer.

BRIEF DESCRIPTION OF THE DRAWINGS Ad

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
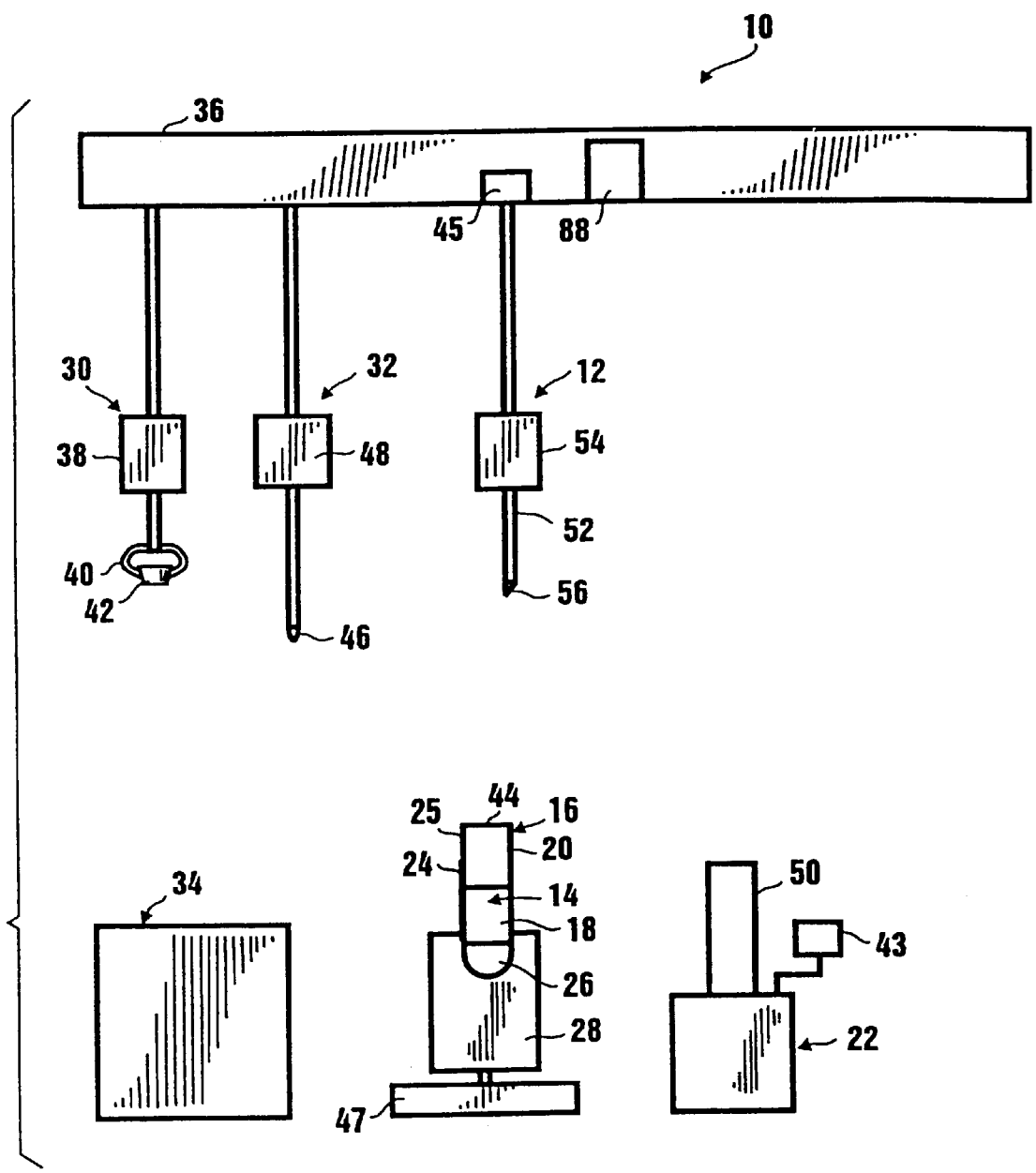
FIG. 1 is an illustration of a device having features of the present invention.

Referring initially to FIG. 1, a device 10 according to the present invention includes an optical probe 12 for preliminarily testing a sample 14 directly in a sample container 16. The device 10 is particularly useful for performing a preliminary test on a neat serum sample 18 directly in a primary collection tube 20 without removing the neat serum sample 18 from the primary collection tube 20.

In one version of the present invention, the optical probe 12 evaluates the integrity of the sample 14 directly in the sample container 16. This allows the laboratory to determine whether the sample 16 is suitable for additional testing with a clinical analyzer 22 and allows the laboratory to evaluate the quality of the results from the clinical analyzer 22. In another version, the optical probe 12 evaluates the volume of sample 14 in the sample container 16. This allows the laboratory to properly allocate the sample 14 available.

In the embodiments illustrated herein, the sample container 16 is the primary collection tube 20 which is used to collect the sample 14 from the patient (not shown). The primary collection tube 20 illustrated in FIG. 1 includes a container label 24 secured to a side 25 of the primary collection tube and a separation gel 26 at the bottom of the primary collection tube 20. The container label 24 contains information about the patient. The type and size of container label 24 can be varied. The separation gel 26 is used to separate cells from serum in the serum sample 18 during centrifugation. The primary collection tube 20 is retained in position by a container holder 28.

The present invention can be adapted to function with sample containers 16 other than the primary collection tube 20, without the container label 24 and/or without the separation gel 26. Additionally, the device 10 may be used for performing preliminary tests on other biological samples such as, urine or cerebral spinal fluid.

FIG. 1 also illustrates that the device 10 can include a number of additional features. For example, the device 10 can include a gripper probe 30, a transfer probe 32, a waste receptacle 34, the clinical analyzer 22, and a probe mover 36. The gripper probe 30, the transfer probe 32 and the optical probe 12 are illustrated as separate units for clarity. Alternately, for example, the gripper probe 30, the transfer probe 32 and/or the optical probe 12 can be combined into a single unit.

In the embodiment illustrated in FIG. 1, the gripper probe 30 includes a gripper controller 38 which controls gripper fingers 40 which grip a container lid 42 on the sample container 18. The container lid 42 is used to selectively enclose a container inlet 44 of the sample container 16. In this embodiment, the gripper probe 30 removes the container lid 42 so that the optical probe 12 can perform the preliminary tests. Subsequently, the gripper probe 30 can reposition the container lid 42 back in the container inlet 44 or dispose of the container lid 44 in the waste receptacle 34. Additionally, the gripper probe 30 can grab the sample container 16 and move the sample container 16 to another location, depending upon the results of the preliminary tests. For example, once the integrety of the sample 14 is determined, depending on the results, the sample 14 and the sample container 16 can be transferred by the gripper probe 30 to the clinical analyzer 22 for further testing or to the waste receptacle 34 for disposal.

The transfer probe 32 includes a transfer probe lumen 46 and an aspirator 48, i.e. motorized syringe, for drawing the sample 14 into or expelling the sample 18 from the transfer probe lumen 46. This feature allows the transfer probe 32 to transfer the sample 14 from the sample container 16 to the appropriate location based upon the results of the preliminary tests with the optical probe 12. For example, once the integrety of the sample 14 is determined, depending on the results, the sample 14 can be transferred by the transfer probe 32 to a cuvette 50 for the clinical analyzer 22 for additional testing, or a container (not shown) for a sample splitter (not shown).

The clinical analyzer 22 includes one or more optical systems 43 to perform additional testing on the sample 14. A clinical analyzer 22 sold by the assignee of the present invention, under the trademark Synchron CX®7, can be utilized with the present invention. One key advantage of this invention is that it increases the throughput of a clinical analyzer 22 by determining if the sample 14 is suitable for testing prior to handling of the sample 14.

The probe mover 36 selectively allows the optical probe 12 to move relative to the sample container 16. This allows the optical probe 12 to be positioned near the sample container 16. For example, the probe mover 36 can be a robotic arm or crane moved by a stepper motor which precisely moves the optical probe 12 to the proper position near the sample container 16. The probe mover 36 preferably includes a monitor 45, such as an encoder, which precisely monitors the relative position of the optical probe 12. The same probe mover 36 or additional probe movers (not shown) can be utilized for moving the gripper probe 30 and/or the transfer probe 32. Alternately, a container mover 47 can precisely move the container holder 28 and the sample container 16 relative to the optical probe 12 and/or the container mover 47 can move the container holder 28 and the sample container 16 to the analyzer 22.

Figure 2:
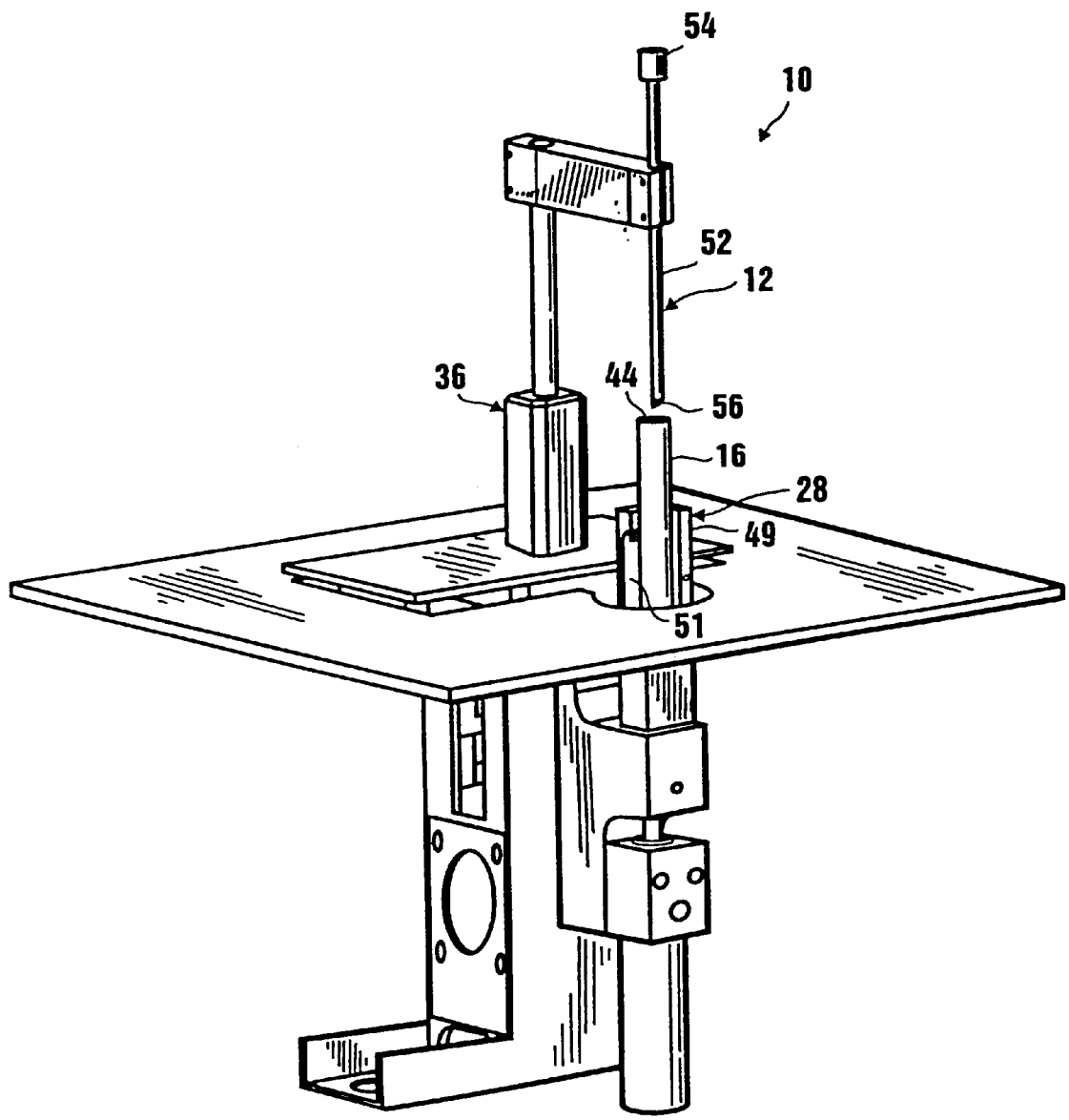
FIG. 2 is a perspective view of a device having features of the present invention.

FIG. 2 illustrates another embodiment of a device 10 having features of the present invention. In this embodiment, the container holder 28 includes a "V" shaped bracket 49 and a clamp 51 which forces the sample container 16 against the bracket 49. Alternately, for example, the container holder 28 could include a flexible boot (not shown) which is activated with a pneumatic cylinder. For the preliminary tests provided herein, it is important that the container holder 28 retain the sample container 16 in the appropriate, known, position and with the appropriate sample container 16 orientation. Additionally, in the embodiment illustrated in FIG. 2, the optical probe 12 is precisely moved relative to the sample container 16 with the probe mover 36.

A number of alternate embodiments of optical probes 12 are illustrated in the Figures. In each embodiment illustrated, the optical probe 12 performs one or more preliminary tests on the sample 14. For example, the optical probe 12 can perform a screening test on the sample 14 to evaluate whether the sample 14 is suitable for additional testing with the analyzer 22 and/or a volume test on the sample 14 to measure the amount of the sample 14 in the sample container 16.

During a screening test, the optical probe 12 evaluates the integrity of the sample 14 while the sample 14 is in the sample container 16. More specifically, during the screening test, the optical probe 12 can determine whether an Interferant is present in the sample 14. Further, the optical probe 12 can determine whether one or more of the Serum Variables such as hemolysis, icterus, and/or lipemia are present in the sample 14. Additionally, the optical probe 12 can also establish one or more of the serum indices, such as a hemolytic index, an icteric index and a lipemic index for the sample 14. These serum indices allow the laboratory to determine whether the sample 14 is suitable for testing with the clinical analyzer 22 and allow the laboratory to the evaluate the quality of the results from the clinical analyzer 22. Thus, with the present invention, the integrity of the neat serum sample 18 is evaluated prior to removing the neat serum sample 18 from the primary collection tube 20.

Additionally or alternately, the optical probe 12 can perform a volume test on the sample 14 in the sample container 10. This allows the laboratory to properly allocate the sample 14 available for subsequent testing.

Generally, the optical probe 12 includes a probe body 52 and one or more detectors 54. Typically, the probe body 52 is generally cylindrical shaped and includes a probe tip 56. The probe body 52 is moved by the probe mover 36 so that the probe tip 56 of the probe body 52 is positioned near the sample container 16 and the sample 14. Alternately, for example, the sample container 16 can be moved relative to the probe body 52 with the container mover 47 so that the probe body 52 is positioned near the sample 14.

The detector 54 can be implemented in a number of alternate ways. For example, the detector 54 can include a single photodiode detector, a photodiode detector array or any other spectrometer which performs a spectrophotometric analysis on the colorimetric information of optical absorbence and/or reflectance of the sample 14 in the sample container 16. With this information, the detector 54 is able to estimate the serum indices for the sample 14. Additionally, while moving the probe body 52 relative to the sample 14 and collecting spectral information, the detector 54 can determine the level and/or volume of the sample 14 in the sample container 16.

Figure 3:
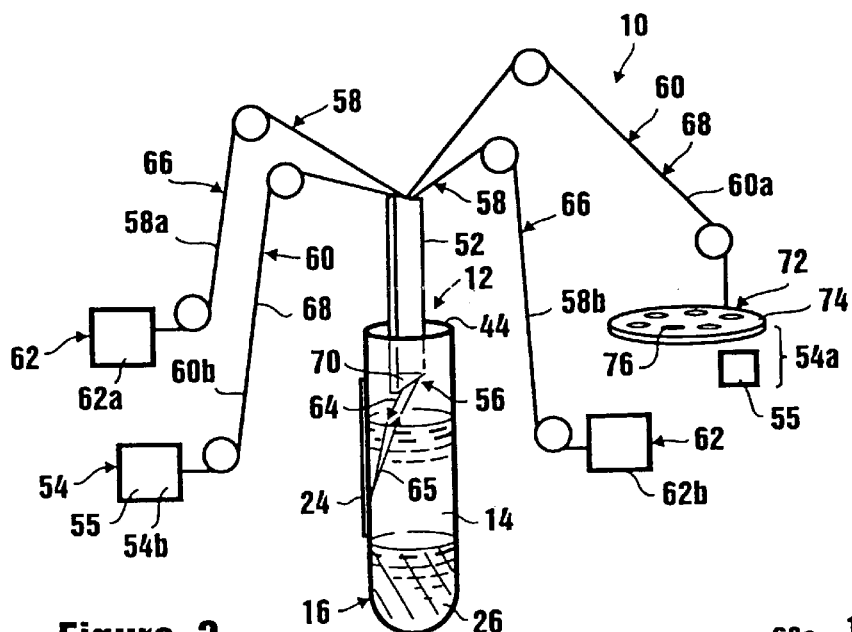
FIG. 3 is an illustration of a portion of a device having features of the present invention.
Figure 4:
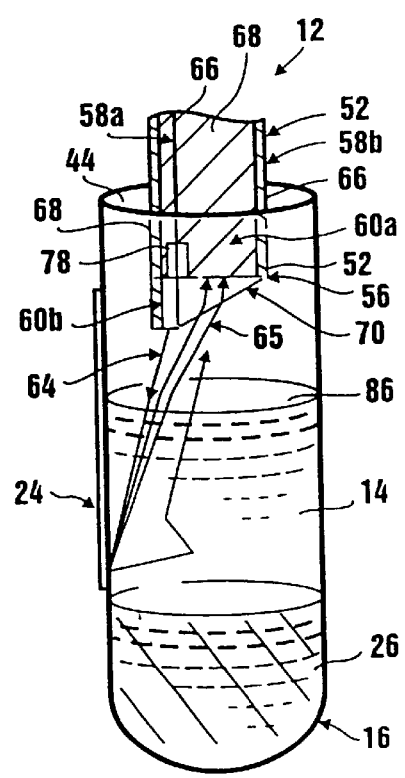
FIG. 4 is a perspective view, in partial cutaway, of a sample container and a portion of an optical probe.
Figure 5:
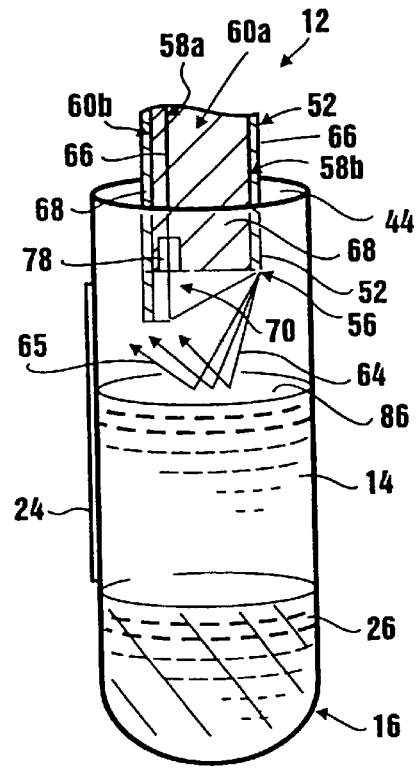
FIG. 5 is a perspective view, in partial cutaway, of a sample container and a portion of an optical probe.

Referring to FIGS. 3–5, the optical probe 12 also includes one or more inputs 58 and one or more collectors 60. Each input 58 typically includes a light source 62 providing an illumination beam 64 which is to be directed towards the sample 14. The light source 62 can be an LED, a laser diode or a continuous light source such as a xenon lamp, a halogen lamp or tungsten lamp. The light source 62 can be stabilized by feedback control (not shown) or calibration of the light source 62 can be performed. Each input 58 typically also includes an input optical fiber bundle 66 which guides the illumination beam 64 from the light source 62 to the probe tip 56. Depending upon the design requirements, each light source 62 can be secured to the probe body 52 or connected to the probe body 52, with the input optical fiber bundle 66. Each collector 60 typically includes a collector optical fiber bundle 68 which transports the incoming information, i.e. collection light 65 from the probe tip 56 to the detector 54. Depending upon the design requirements, the detector 54 can be secured to the probe body 52 or connected to the probe body 52 with the collector optical fiber bundle 68.

In the embodiment illustrated in FIGS. 3–5, the optical probe 12 performs both a screening test and a volume test on the sample 14. In this embodiment, the optical probe 12 includes a prism 70 near the probe tip 56, a first input 58a, a second input 58b, a first collector 60a and a second collector 60b. The first input 58a and the first collector 60a are used for the screening test while the second input 58b and the second collector 60b are used for the volume test.

The prism 70 is made of a transparent material such as glass. The prism 70 illustrated in FIG. 3–5 has a cross-section which approximately forms a 30–40 degree right triangle. The upper limit of the angle of the prism 70 is limited by the total internal reflection at the exit face of the prism 70. The upper limit of the prism angle is approximately 41 degrees for a prism 70 made of BK7 glass. The lower limit of the angle is selected to provide a reasonable entrance angle of the illumination beam 64 to the sample 14 and to avoid the cells and separation gel 26 in the sample container 16. An epoxy optical glue (not shown) and/or other attachment means can be used to attach the prism 70 to the probe body 52. The prism 70 can be coated with an anti-reflection coating (not shown).

As can best be seen with reference to FIGS. 3 and 4, the optical probe 12 is positioned within the container inlet 44 above the sample 14 during the screening test. In this embodiment, the first input 58a includes the input optical fiber bundle 66 and the light source 62a. The prism 70 bends the illumination beam 64 from the first input 58a relative to the probe body 52 so that the illumination beam 64 is directed towards the container label 24. The first collector 60a includes the collector optical fiber bundle 68. The first collector 60a receives the light 65 reflected off of the container label 24 and/or the sample 14 and transfers the information to a first detector 54a.

In this embodiment, the calorimetric or spectral information of the scattered light 65 is analyzed by the first detector 54a to determine if the sample contains an interferant, to determine the presence of one or more of the serum variables and/or establish one or more of the serum indices. More specifically, the light 65 from the sample 14 carries particle scattering information, as in a lipemic sample, and absorbance information, as in a hemolytic or icteric sample, or a combination of the two. From the information collected, the first detector 54 performs the screening test. Stated another way, the spectral information is analyzed by the first detector 54a to determine if the sample contains an interferant, to determine whether any of the serum variables are present in the sample 14 and/or to establish the serum indices.

Once the serum indices are determined, depending on the results, the sample 14 can be transferred to the clinical analyzer 22 for further testing or to the waste receptacle 34 for disposal. Typically, the detector 54 will print or display the results from the preliminary test so that the laboratory can evaluate what to do with the sample 14.

Referring back to FIG. 3, the first detector 54a utilizes a filter wheel 72 in addition to a photodiode 55 to perform the screening test. The filter wheel 72 includes a rotating wheel 74 with different bandpass filters 76 secured thereto. The filter wheel 72 is rotated so that the information collected by the first collector 60a passes through multiple different filters 76 to the photodiode 55. The bandpass filters 76 provide spectral discrimination of the information transferred to the photodiode 55.

Alternately, the first detector 54a can be any spectrometer and/or array detector which performs a spectroscopic analysis. In yet another alternate embodiment, a filter wheel (not shown) can be inserted after the light source 62, before the sample 14, to provide a colored (finite wavelength) illumination beam 64. The light collected by the first collector 60a can then be directly analyzed by the photodiode 55.

Figure 6:
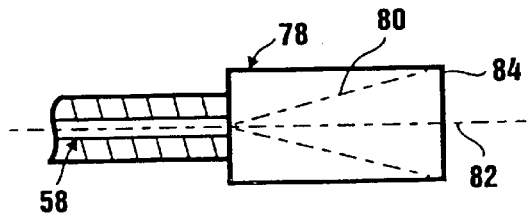
FIG. 6 is an exploded cut-away view of a lens having features of the present invention.

Additionally, the optical probe 12 illustrated in FIGS. 3–5 utilizes a lens 78 near the probe tip 56 to collimate and/or focus the illumination beam 64 from the first input 58a. FIG. 6 illustrates an enlarged cross-sectional view of a lens 78 suitable for use in the present invention. The lens 78 collimates the illumination beam 64 (not shown in FIG. 6) from the input 58 to improve light reflectance and absorbance. The lens 78 is a ¼ wavelength graded index optical lens. These devices are manufactured such that the index of refraction of the lens 78 is parabolic, and has a decreasing index of refraction as a function of its radius as measured from a center 82 of the lens 78. With this design, light ray 80 travels faster at an edge 84 of the lens 88 than at the center 82 of the lens 78. The index of refraction and the length of the lens 78 is designed to give substantially the same amount of light path for the illumination beam 64 from the center 82 to the edge 84 of the lens 78. This allows the illumination beam 64 at the end of the lens 78 to be collimated. Alternately, lens 78 can be replaced by another collimating and/or focusing device.

FIG. 3 and 5 illustrates how a volume and/or level test can be performed on the sample 14 with the optical probe 12. As provided above, the second input 58b and the second collector 60b are used to perform the volume test to determine the amount of sample 14 in the sample container 16. The second input 58b includes light source 62b and the input optical fiber bundle 66 while the second collector 60b includes the collector fiber bundle 68. In this embodiment, the second input 58b is positioned at an outer edge of prism 70 and the light of input 58b is bent at a slight angle by the prism 70. The second collector 60b is positioned outside of the prism 70 to minimize the effects of the prism 70.

As illustrated in FIG. 5, the second input 58b directs the illumination beam 64 at an upper sample surface 86 of the sample 14 at a slight angle from normal. The reflected light 65 is collected by the second collector 60b and transferred to a second detector 54b (shown in FIG. 3). The level of the sample surface 86 is determined by monitoring the second detector 54b while moving the probe body 52 and the sample container 16 together or apart, i.e. distance between the sample surface 86 and the probe 12 is increased or decreased. The strength of the light 65 received by the second collector 60b is strongest when the second collector 60b receives light reflected directly off of the sample surface 86 of the sample 14. This occurs when the second input 58b and the second collector 60b are approximately at optical conjugate point above the sample surface 86. Stated another way, the maximum light 65 intensity is observed when the probe tip 56 is at a conjugate location for the reflected light 65 from the sample surface 86.

More specifically, in this embodiment the second input 58b and second collector 60b are mounted near the probe tip 56 and are moved with the probe body 52 by the probe mover 36 (shown in FIG. 1). The probe mover 36 precisely moves the probe body 52 and probe tip 56 and monitors the position of the probe tip 56 with the monitor 45. For this embodiment, the probe mover 36 can move the probe body 52 in a plurality of sequential steps towards the sample 14. As the probe mover 36 moves the probe tip 56 vertically towards the sample 14, the intensity of light 65 collected by the second collector 60b varies. Stated another way, with the probe tip 56 moving downward towards the sample surface 68, the information is processed and intensity of reflected light 65 is determined in real-time. The peak or maximum intensity of observed reflected light 65 determines the level or position of the sample surface 86. Thus, the peak light received is used to locate when the probe tip 56 is one focal length above the sample surface 86. By monitoring the relative position of the probe tip 56 with the probe mover 36, the height of the sample surface 86 in the sample container 16 can be determined. With information regarding the dimensions of the sample container 16, the volume of sample 14 in the sample container 16 can subsequently be determined.

In examples illustrated here, a logic circuit 88 (illustrated in FIG. 1) can control the probe mover 36, process the signal from the second detector 54b and determine the level and/or volume of the sample 14 in the sample container 16. The mover 36 will stop the probe tip 56 when the signal level reaches its maximum, and the position is reported to the logic circuit 88. The final position of the probe tip 56 is this position plus a fixed offset.

Utilizing a relatively fast probe mover 36 which moves the probe body 52 at approximately 10 cm/sec, the position of the sample surface 86 can be established in approximately one second.

Depending on the application, the probe tip 56 can then be moved into a pre-programmed location relative to the sample surface 86 to perform the screening test. In the embodiment illustrated in FIGS. 3–5, the optimized location for the optical probe 12 for the screening test can be located with the monitor 45 and/or with the second input 58b and the second collector 60b.

Typically, in the embodiment illustrated in FIGS. 3 and 5, during the preliminary tests, the probe tip 56 is positioned by the probe mover 36 (shown in FIG. 1) within the container inlet 44 of the sample container 16 and between approximately 2 and 5 millimeters above the sample surface 86. Accordingly, the probe tip 56 does not contact the sample 14, the probe tip 56 does not affect the integrity of the sample 14 and the probe tip 56 does not have to be washed to prevent carryover between samples. Thus, the optical probe 12 performs a non-invasive, preliminary screening examination of the sample 14. This saves on the cost and disposal of wash fluid (not shown) and eliminates carry-over between consecutive samples. In high volume testing applications, the reduced waste fluid can result in reduced processing costs, as well as increased ability to comply with environmental regulations.

As will become evident from the examples provided below, the geometry of the optical probe 12 including the positions of the input(s) 58 and the collection(s) 60 can be modified to alter and/or enhance the sensitivity of the detector 54.

Figure 7:
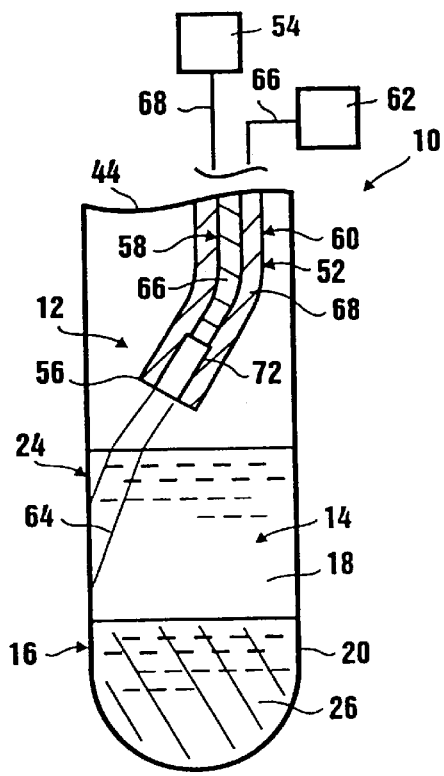
FIG. 7 is a side plan view, in partial cut-away, of another embodiment of a portion of an optical probe and a sample container having features of the present invention.

FIG. 7 illustrates another embodiment of an optical probe 12 and the sample container 16 used for performing a screening test. In this embodiment, the probe tip 56 of the optical probe 12 is again positioned within the container inlet 44 of the sample container 16 above the sample 14. The input 58 includes input optical fiber bundle 66 and a light source 62. The collector 60 includes a tubular collector optical fiber bundle 68 which encircles the input optical fiber bundle 66. The probe body 52 is bent near the probe tip 56 so that the illumination beam 68 is directed towards and illuminates the container label 24.

The collector 60, in this embodiment, also receives light 65 (not shown in FIG. 7) reflected off of the container label 24 on the sample container 16. The spectral and/or colorimetric information of the scattered light 65 is analyzed by the detector 54 to determine if an interferant is present in the sample 14, to determine the presence of the serum variables and/or establish the serum indices. The optical probe 12 illustrated in FIG. 7 also utilizes a lens 78, similar to the lens 78 illustrated in FIG. 6, near the probe tip 56 to collimate and/or focus the illumination beam 64.

Figure 8:
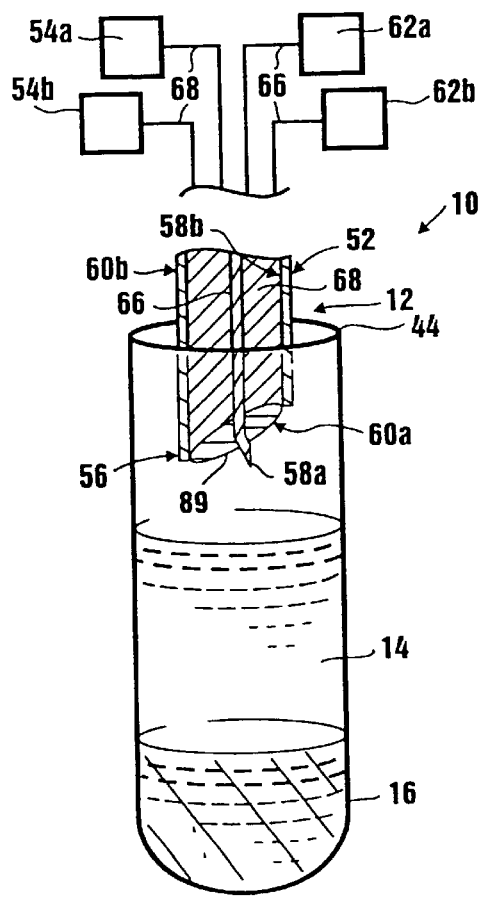
FIG. 8 is a side plan view, in partial cut-away, of another embodiment of a portion of an optical probe and a sample container having features of the present invention.

FIG. 8 illustrates another embodiment of the present invention. In this embodiment, the optical probe 12 performs both a screening test and a volume test. More specifically, the optical probe 12 includes a first input 58a and a first collector 60a for performing the screening test and a second input 58b and a second collector 60b for performing a volume test. The first input 58a includes the input optical fiber bundle 66 and the first light source 62a. The first collector 60a receives the light 65 (not shown in FIG. 8) reflected from the sample 14. The first collector 60 includes the tubular collector fiber bundle 68 which encircles the input optical fiber bundle 66 and a baffle 89 inserted in the collector optical fiber bundle 68 near the probe tip 56 to suppress stray light. A tip of the first collector 60a is cut at an angle so that most of the reflected light 65 (not shown in FIG. 8) will be reflected into the opposite side of the collector optical fiber 68. The spectral information is transferred to the first detector 54a and analyzed to determine if an interferant is present, to determine the presence of the serum variables and/or establish the serum indices.

The second input 58b and the second collector 60b are used to perform the volume test so that the amount of sample 14 in the sample container 16 can be determined. In this embodiment, the second input 58b and the second collector 60b are positioned on extreme edges of the probe tip 56. As provided above, the intensity of light 65 received by the second collector 60b and transferred to the second detector 54b is maximum when the illumination area is at the sample surface 86 and the collector 60b is viewing directly the reflected light from the sample surface 86. This peak signal is utilized to locate the sample surface 86. With the location of the sample surface 86 and the dimensions of the sample container 16, the volume of sample 14 available for testing can be determined.

Figure 9:
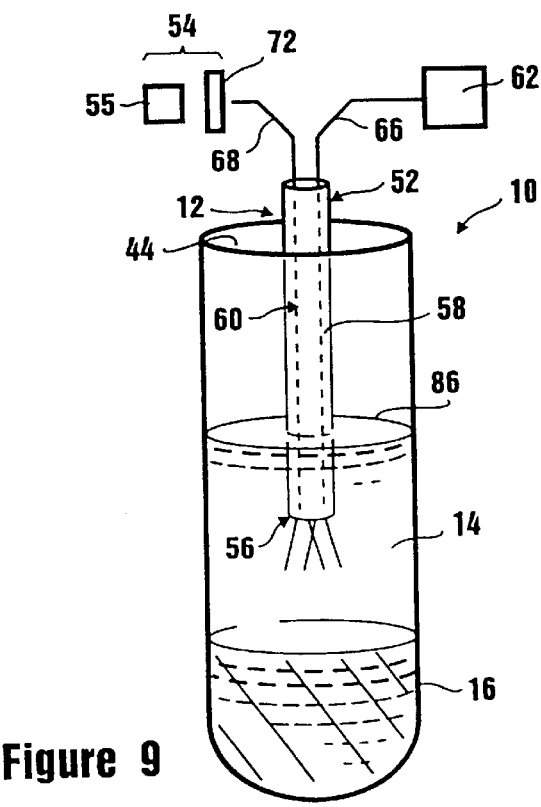
FIG. 9 is a perspective view of another embodiment of a portion of a optical probe and a sample container having features of the present invention.

Another embodiment of the present invention is illustrated in FIG. 9. In this embodiment, the probe tip 56 is illustrated a few millimeters below the sample surface 86 of the sample 14. The optical probe 12 includes a single input 58 and a single collector 60. The input 58 again includes an input optical fiber bundle 66 and a light source 62. The collector 60 includes collector optical fiber bundle 68. In this embodiment, the input optical fiber bundle 66 and the collector optical fiber bundle 68 are each approximately 1 millimeter in diameter and spaced apart approximately 1 millimeter. The input optical fiber bundle 66 and the collector optical fiber bundle 68 in this example, each have a flat tip, which can be easily modified to other optical arrangements to enhance the signal sensitivity. The detector 54 includes the photodiode 55 and filter wheel 72. In this embodiment, the input 58 and the collector 60 can be used to perform the volume test during movement of the probe body 52 into the sample container 16 towards the sample surface 86. Subsequently, with the probe tip 56 below the sample surface 70, the input 58 the collector 60 and the detector 54 can be used for the screening test.

Figure 10:
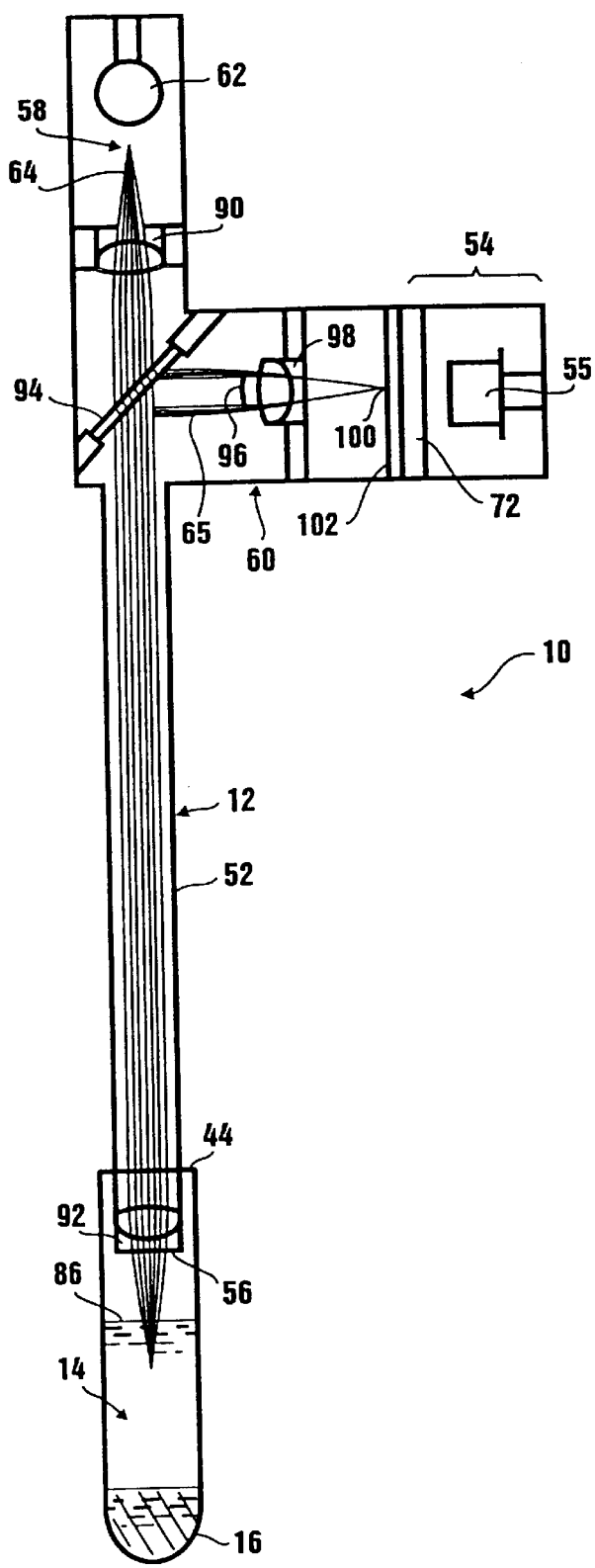
FIG. 10 is a cut-away view of another embodiment of an optical probe and a sample container having features of the present invention.

FIG. 10 illustrates yet another embodiment of an optical probe 12 having features of the present invention. In FIG. 10, the optical probe 12 includes an input 58 and a collector 60 which are used to perform the screening test and the volume test. More specifically, the input 58 includes a light source 62 which directs an illumination beam 64 through an upper lens 90 and a lower lens 92 into the sample 14. The collector 60 includes a beamsplitter 94, a blocker 96, a third lens 98, and a pinhole 100 in a wall 102. In this embodiment, the absorbed and scattered light 65 from the sample 14 is collected by the lower lens 92 and directed by the optical beamsplitter 94 towards the third lens 98. The blocker 96 is positioned between the beamsplitter 94 and the third lens 98 to block light directed towards the center of the third lens 98. Light 65 which travels through the third lens 98 must pass through the pinhole 100 in the wall 102 to get to the detector 54. In this design, the intense reflected light 65 from the sample surface 86 is blocked by the combination of the blocker 96 at the center of the third lens 98 and the pinhole 100 in front of the detector 54. With this design, the blocking power increases by increasing the size of the blocker 90 and decreasing the size of the pinhole 92.

The information which passes through the pinhole 100 goes through a filter wheel 72 into a photodiode 55. Based on the information received, the detector 54 can perform the screening test. Further, during movement of the probe tip 56 within the sample container 16, the detector 54 can monitor for the peak signal to perform the volume test.

Figure 11:
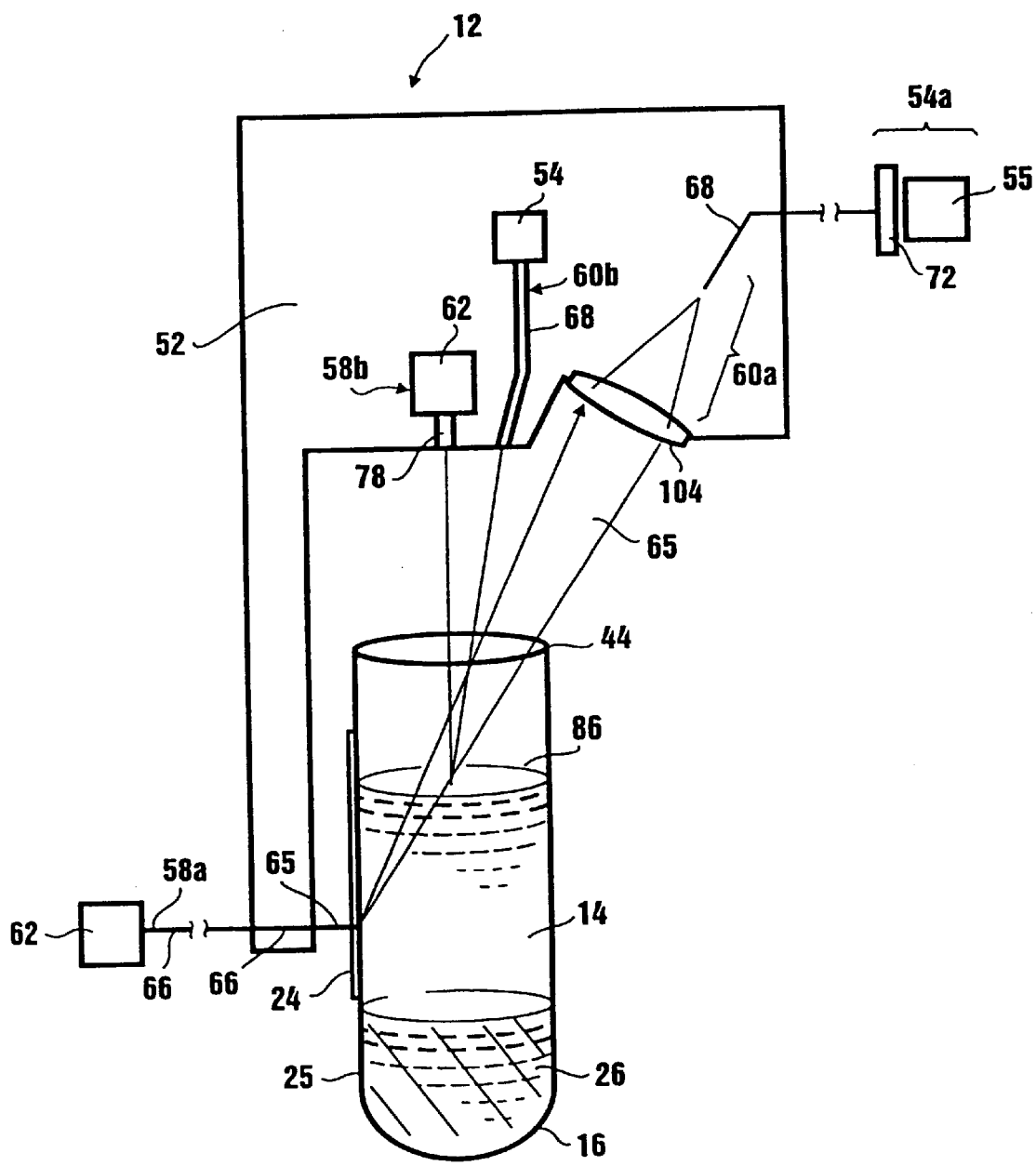
FIG. 11 is a side plan view of another embodiment of an optical probed and a sample container having features of the present invention.

FIG. 11 is a schematic illustration of yet another embodiment having features of the present invention. In this embodiment, the optical probe 12 includes a first input 58a, a second input 58b, and a first collector 60a and a second collector 60b. The first input 58a includes the light source 62 and the input optical fiber bundle 66. The first input 58a is moved to the side 25 of the sample container 14 so that the first input 58a can illuminate the side 25 and/or the container label 24 of the sample container 14. The light 65 diffuses into the sample 14 and is collected by the first collector 60a. The first collector 60a includes a collector lens 104 and a collector optical fiber bundle 68 for transferring the information to the first detector 54a. The first detector 54a utilizes a filter wheel 72 and a photodiode 55 to perform the screening test. The second input 58b includes a light source 62 for illuminating the sample surface 86 and a lens 78 collimating the light from the light source 62. In this embodiment, each collector optical fiber bundle 68 is preferably, approximately 1 millimeter in diameter to reduce stray light. In this embodiment, the second detector 54b is used to position the optical probe 12 in the proper position. In the embodiment illustrated in FIG. 11, the input optical fiber bundle 66 for the first input 58a, the second input 58b, the collector optical fiber bundle 68 for the first collector 60a and the second collector 60b are all secured to a single probe body 52. Alternately, for example, the various components in this embodiment can be separated into multiple probe bodies which move independently of each other.

Importantly, in the embodiments provided herein, the affect of the different materials for the sample container 14, the container label 24 and/or the separation gel 26 can be calibrated out of the system. Thus, for example, the present invention can be utilized without the container label 24 and/or the separation gel 26. Alternately, the size and/or type of container label 24 can be varied.

With most of the embodiments provided herein, the probe tip 56 is positioned within the container inlet 44 of the sample container 16. Thus, access to the side 25 of the sample container 16 is not necessary. Further, most of the embodiments illustrated herein are non-invasive. Stated another way, in most embodiments, the probe tip 56 is positioned above the sample 44. Thus, the probe tip 56 will not adversely affect the integrity of the sample 14 and the probe tip 56 does not have to be washed to prevent carryover between samples 14. This saves on the cost and disposal of the wash fluid and reduces carry-over between consecutive samples 14. In high volume testing applications, the reduced waste fluid can result in reduced processing costs, as well as increased ability to comply with environmental regulations.

OPERATION

An example of the operation of one embodiment of an optical probe 12 having features of the present invention can best be visualized with reference to FIGS. 1 and 3–5. The operation can begin with the gripper probe 30 moving the sample container 14 to the container holder 28 and subsequently removing the container lid 42 from the sample container 16. Next, the probe mover 36 moves the optical probe 12 and/or the container mover 47 moves the sample container 16 so that the optical probe tip 12 is approaching the sample container 16. With particular reference to FIGS. 3 and 5, with the optical probe 12 approaching the sample container 16, the second light source 62b is activated so that the second input 58b directs the illumination beam 65 towards the sample surface 86. The second collector 60b receives the incoming light 65 and the second detector 54b monitors for the peak signal. When the peak signal is detected, the monitor 45 (see FIG. 1) transfers information regarding the position of the optical probe 12 to the logic circuit 88 (see FIG. 1). Next, the logic circuit 88 determines the position or level of the sample surface 86. With this information, the volume of sample 14 in the sample container 16 can be determined. The second light source 62b is subsequently deactivated.

Next, with particular reference to FIGS. 3 and 4, the first light source 62a is activated and directs an illumination beam 64 into the sample 14 directed towards the container label 24. The first collector 60a then collects the light 65 which is reflected off of the label 24. Measurements are transferred to the first detector 54a. From these measurements, the first detector 54a determines whether hemolysis, icteris and lipemia are present in the sample 14. Preferably, from these measurements, the first detector 54a also estimates the hemolytic index, the icteric index and the lipemic index in the sample 14.

Preferably, the sample 14 is transferred to either the waste receptacle 34 or the cuvette 50 of the clinical analyzer 22 based upon the measurements from the detector 56. For example, if one of the serum indices is above a predetermined value, the probe mover 36 moves the gripper probe 30 to grip and move the sample container 16 to the waste receptacle 34. Alternately, if all the serum indices are below the predetermined value, the probe mover 36 moves the transfer probe 32 so that sample 14 is transferred to the clinical analyzer 22.

As previously mentioned, the predetermined value varies according to the scale of the serum indices, which of the serum indices is in question, and the tests to performed by the clinical analyzer or other device. For example, if the hemolytic index, the icteric index and the lipemic index are rated on a scale of 0–4, and a value of 3 for the hemolytic index, a value of 2 for the icteric index or a value of 2 for the lipemic index could effect the results from a particular clinical analyzer, the predetermined value of the hemolytic index is 3, the predetermined value for the icteric index is 2 and the predetermined value for the lipemic index In this situation, if the first detector 54a determines that the hemolytic index is 3, the sample container 16 and sample 14 would be transferred by the gripper probe 30 to the waste receptacle 34. Alternately, if the hemolytic index is only two (2), the isoteric index is one (1) and the limeric index is (one) (1), the sample 14 would be suitable for testing and the sample 17 could be moved with the transfer probe 32 to the cuvette 50 of the analyzer 22.

While the particular device 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for preliminarily testing a neat serum sample contained in a primary collection tube, the method comprising the steps of:

collecting the neat serum sample from a patient into a primary collection tube;

positioning an optical probe over the primary collection tube above or below the serum sample surface;

directing an illumination beam through the sample towards a container label on the primary collection tube; and receiving a light beam reflected off the label to monitor the sample for determining the suitability of the neat serum sample for additional testing.

2. The method of claim 1 wherein the step of monitoring the neat serum sample includes the step of determining whether an interferant is present in the neat serum sample in the primary collection tube.

3. The method of claim 1 wherein the step of monitoring the neat serum sample includes the step of determining whether at least one of the serum variables is present in the neat serum sample in the primary collection tube.

4. The method of claim 3 wherein the step of monitoring the neat serum sample includes the step of determining whether hemolysis, icterus and lipemia are present in the neat serum sample in the primary collection tube.

5. The method of claim 1 wherein the step of monitoring the neat serum sample includes the step of determining at least one of the serum indices of the neat serum sample in the primary collection tube.

6. The method of claim 5 wherein the step of monitoring the neat serum sample includes the step of determining a hemolytic index, an icteric index and a lipemic index of the neat serum sample in the primary collection tube.

7. The method of claim 1 wherein the step of monitoring the neat serum sample includes the step of determining the volume of neat serum sample in the primary collection tube.

8. The method of claim 1 wherein the step of monitoring the neat serum sample includes the step of determining the level of the neat serum sample in the primary collection tube.

9. The method of claim 1 including the step of moving the primary collection tube relative to the optical probe so that the optical probe is positioned near the primary collection tube.

10. The method of claim 1 including the step of moving the optical probe relative to the primary collection tube so that the optical probe is positioned near the primary collection tube.

11. The method of claim 1 further comprising the step of transferring the sample to a receptacle based upon suitability of the sample for additional testing.

12. The method of claim 11 wherein the step of transferring the sample comprises transferring the sample to an analyzer for further testing.

13. The method of claim 1, wherein the step of monitoring comprises positioning the probe, below a sample surface.

14. The method of claim 1, wherein the step of monitoring comprises positioning the probe above a sample surface.

15. A device for performing a preliminary screening test on a neat serum sample in a primary collection container, the device comprising an optical probe, the optical probe including (i) a probe body which is adapted to be moved relative to the sample container and to be positioned above or below the sample surface, (ii) a collector which is secured to the probe body and is adapted to receive information from the sample without removing the sample from the primary collection container, and (iii) a detector electrically connected to the collector, the detector receiving information from the collector and performing a preliminary test on the sample contained in the container to determine the suitability of the sample for additional testing wherein the optical probe includes an input for directing an illumination beam through the sample towards a container label on the sample container and wherein the collector receives a light beam reflected off the label.

16. The device of claim 15 wherein the detector determines whether an interferant is present in the sample in the sample container.

17. The device of claim 15 wherein the detector determines whether at least one of the serum variables is present in the sample in the sample container.

18. The device of claim 15 wherein the detector establishes at least one of the serum indices for the sample in the sample container.

19. The device of claim 15 wherein the detector determines the volume of the sample in the sample container.

20. The device of claim 15 wherein the detector determines the level of the sample in the sample container.

21. The device of claim 15 further comprising a mover adapted for moving the sample container relative to the optical probe so that the probe body is positioned near the sample container.

22. The device of claim 15 further comprising a mover adapted to move the optical probe relative to the sample container so that the probe body is positioned near the sample container.

23. The device of claim 15 further comprising a mover which is adapted to move at least a portion of the sample from the sample container to an analyzer for additional testing.

24. A clinical analyzer including the device of claim 15.

25. The device of claim 15 further comprising a light source for generating a beam of light and an input optical fiber bundle for directing the beam toward the sample.

26. The device of claim 25, wherein the light source is selected from the group consisting of: LED, laser diode, xenon lamp, halogen lamp, and tungsten lamp.

27. The device of claim 15, further comprising a lens disposed near a sample-facing end of the probe, for collimating and focusing the beam of light generated by the input.

28. The device of claim 15, wherein the collector comprises a collector optical fiber bundle, the device further comprising a baffle disposed in the collector optical fiber bundle to suppress stray light.

29. The device of claim 15 further comprising a blocking assembly for blocking a high-intensity portion of the reflected light.

* * * * *